United States Patent
Ou et al.

(10) Patent No.: US 8,314,932 B2
(45) Date of Patent: Nov. 20, 2012

(54) SURFACE-ENHANCED RAMAN SPECTROSCOPY DEVICE AND A MOLD FOR CREATING AND A METHOD FOR MAKING THE SAME

(75) Inventors: Fung Suong Ou, Mountain View, CA (US); Zhiyong Li, Redwood City, CA (US); Min Hu, Sunnyvale, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 310 days.

(21) Appl. No.: 12/771,440

(22) Filed: Apr. 30, 2010

(65) Prior Publication Data

US 2011/0267606 A1 Nov. 3, 2011

(51) Int. Cl.
*G01J 3/44* (2006.01)
(52) U.S. Cl. ........................................................ 356/301
(58) Field of Classification Search .................. 356/301
See application file for complete search history.

(56) References Cited

U.S. PATENT DOCUMENTS

| | | |
|---|---|---|
| 7,224,451 B2 | 5/2007 | Naya |
| 7,288,419 B2 | 10/2007 | Naya |
| 7,351,588 B2 | 4/2008 | Poponin |
| 7,476,787 B2 | 1/2009 | Thomas et al. |
| 7,576,854 B2 | 8/2009 | Wang et al. |
| 7,586,601 B2 | 9/2009 | Ebstein |
| 7,609,378 B2 | 10/2009 | Konakahara |
| 7,651,863 B2 | 1/2010 | Hulteen et al. |
| 7,656,525 B2 | 2/2010 | Zhao et al. |
| 7,707,647 B2 | 4/2010 | Konakahara |
| 2001/0006869 A1 | 7/2001 | Okamoto et al. |
| 2004/0135997 A1 | 7/2004 | Chan |
| 2006/0250613 A1 | 11/2006 | Demuth |
| 2007/0015288 A1 | 1/2007 | Hulteen |
| 2007/0086001 A1 | 4/2007 | Islam |
| 2007/0115469 A1 | 5/2007 | Ebstein |
| 2008/0079104 A1 | 4/2008 | Stewart et al. |
| 2009/0033929 A1* | 2/2009 | Mazur et al. ................... 356/301 |
| 2009/0117646 A1 | 5/2009 | Stordeur et al. |
| 2010/0062226 A1 | 3/2010 | Hulteen |
| 2010/0109203 A1* | 5/2010 | Chen et al. ..................... 264/446 |
| 2010/0321684 A1* | 12/2010 | Bratkovski et al. ............ 356/301 |
| 2011/0128536 A1* | 6/2011 | Bond et al. ..................... 356/301 |

(Continued)

FOREIGN PATENT DOCUMENTS

WO WO-2006138442 12/2006

(Continued)

OTHER PUBLICATIONS

Schmidt et al., "Towards Easily Reproducible Nano-Structured SERS Substrates", IEEE Sensors 2009 Conference, pp. 1763-1767.

(Continued)

*Primary Examiner* — Kara E Geisel (57) ABSTRACT

A surface-enhanced Raman spectroscopy device includes a substrate, and an ultraviolet cured resist disposed on the substrate. The ultraviolet cured resist has a pattern of cone-shaped protrusions, where each cone-shaped protrusion has a tip with a radius of curvature equal to or less than 10 nm. The ultraviolet cured resist is formed of a predetermined ratio of a photoinitiator, a cross-linking agent, and a siloxane based backbone chain. A Raman signal-enhancing material is disposed on each of the cone-shaped protrusions.

6 Claims, 5 Drawing Sheets

U.S. PATENT DOCUMENTS

| | | | |
|---|---|---|---|
| 2012/0013903 A1 | 1/2012 | Kuo | |
| 2012/0113419 A1 | 5/2012 | Wang | |
| 2012/0161600 A1* | 6/2012 | Norris et al. | ............ 313/11 |

FOREIGN PATENT DOCUMENTS

| | | |
|---|---|---|
| WO | PCT/US2008/083827 | 11/2008 |
| WO | PCT/US2009/052308 | 7/2009 |
| WO | WO 2009/117646 | 9/2009 |
| WO | WO-2010056258 | 5/2010 |
| WO | WO-2011014176 | 2/2011 |

OTHER PUBLICATIONS

Wu et al., One-Kilobit Cross-Bar Molecular Memory Circuits at 30-nm Half-Pitch Fabricated by Nanoimprint Lithography, Springer-Verlag, Pub online Mar. 11, 2005, pp. 1173-1178.

Hu et al., "Metal Coated Si Nanograss as Highly Sensitive SERS Sensors", Proc. of SPIE, vol. 7312, pp. 731201-1-6, 2009.

Gilles et al., "UV Nanoimprint Lithography with Rigid Polymer Molds", Microeletronic Engineering 86 (2009), pp. 661-664.

He et al.,Lg-Scale Synth of Flex Free-Stand SERS Sub w/ High Sensitivity:Electrospun PVA Nanofibers Embed w/ Cont Align of Silver Nanoparticles,ACSNANO, vol. 3,No. 12,3993-4002, 2009.

Application (PCT/US2008/083827), Nov. 2008.

Application (PCT/US2009/052308).

Cao, et al., "Enhance Raman Scattering from Individual Semiconductor Nanocones and Nanowires", Physical Review Letters PRL 96, 157402, 2006.

PCT Search Report, PCT/US2008/083827.

PCT Search Report, PCT/US2009/052308.

* cited by examiner

SURFACE-ENHANCED RAMAN SPECTROSCOPY DEVICE AND A MOLD FOR CREATING AND A METHOD FOR MAKING THE SAME

STATEMENT REGARDING FEDERALLY SPONSORED RESEARCH OR DEVELOPMENT

This invention was made in the course of research partially supported by grants from the Defense Advanced Research Projects Agency (DARPA), Contract No. HR0011-09-3-0002. The U.S. government has certain rights in the invention.

BACKGROUND

The present disclosure relates generally to surface-enhanced Raman spectroscopy devices, and a mold for creating the same and a method for making the same.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or biological sensing applications. However, the intrinsic Raman scattering process is very inefficient, and rough metal surfaces, various types of nano-antennas, as well as waveguiding structures have been used to enhance the Raman scattering processes (i.e., the excitation and/or radiation process described above). This field is generally known as surface enhanced Raman spectroscopy (SERS).

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 2A through 2I are semi-schematic cross-sectional views which together depict an embodiment of a method for forming an embodiment of the mold, where FIG. 2D is a cross-section taken along line 2D-2D of FIG. 1;

DETAILED DESCRIPTION

Embodiments of the surface-enhanced Raman spectroscopy devices disclosed herein may be fabricated on flexible substrates. The devices are made from a master mold, which can be placed onto a roller that is part of a roller/imprint machine, thus enabling rolls of such devices to be fabricated. As such, the method disclosed herein is scalable so that mass fabrication of the substrates may be achieved. In some instances, the periodicity of the cone-shaped protrusions of the devices may be optimized for sensing within a particular wavelength range and/or for detection of a particular chemical species. In other instances, the cone-shaped protrusions may be formed in non-periodic patterns. The master mold used to form the SERS devices is made from a template having cone-shaped features with sub-10 nm radii of curvature. The material used to make the mold and the final device is a rigid ultraviolet curable resist that is capable of duplicating the ultra-fine details of such features.

As used herein, the terms "cone-shaped" or "cone shape" describe a protrusion, or the negative replica of such protrusion, having a three-dimensional geometric shape that tapers from a round perimeter base to a sharp tip (e.g., an apex or vertex). The sharp tip has a radius of curvature that is equal to or less than 10 nm. The height of such protrusions may be up to 2 µm, and the round perimeter base may have a diameter up to 500 nm.

Figure 1:
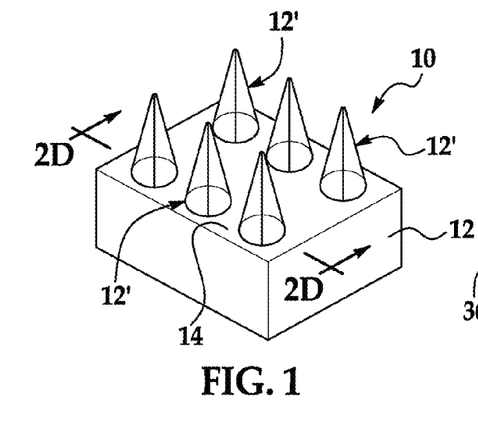
FIG. 1 is semi-schematic perspective view of a silicon cone-shaped substrate that can be used as a template for forming an embodiment of a mold.
Figure 8A:
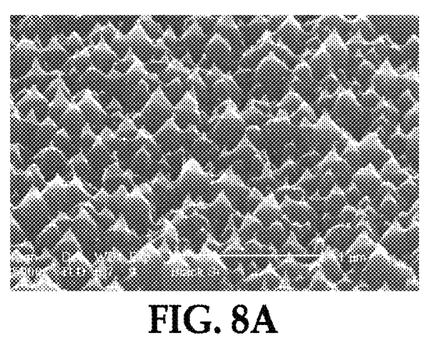
FIGS. 8A and 8B are scanning electron microscope (SEM) images of a silicon cone-shaped substrate at 35000× magnification that was used as a template for forming molds made from polydimethylsiloxane (referred to as "Comparative Mold" in the Example) and from an embodiment of an ultraviolet resist disclosed herein (referred to as "Mold" in the Example)
Figure 8B:
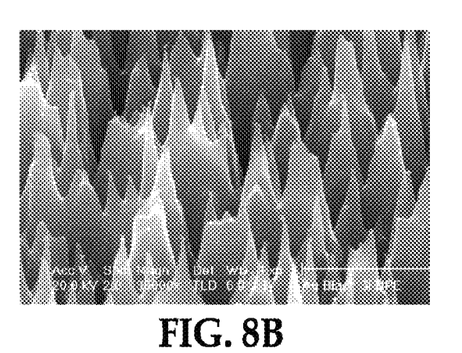

Referring now to FIG. 1, a template 10 used for forming an embodiment of a master mold (shown in FIG. 2H) is depicted. SEM images of an example of the template 10 are also shown in FIGS. 8A and 8B, and will be discussed herein in reference to the Example.

The template 10 includes a substrate 12. Non-limiting examples of suitable substrate 12 materials include single crystalline silicon, polymeric materials (acrylics, polycarbonates, polydimethylsiloxane (PDMS), polyimide, etc.), metals (aluminum, copper, stainless steel, nickel, alloys, etc.), quartz, ceramic, sapphire, silicon nitride, or glass. In some instances, after protrusions 12' are formed on the substrate 12, the incoming light may become trapped by the protrusions 12' by mechanisms such as multiple forward scattering or through continuous variation of the index of refraction. The trapped light renders the appearance of the substrate 12 dark or black. As such, a silicon substrate 12 having the protrusions 12' thereon may be referred to herein as "black silicon". The dimensions of the substrate 12 may vary, depending, at least in part, upon the desirable size of the resulting template 10 and upon the number and depth of the protrusions 12' to be formed.

As shown in FIG. 1, the substrate 12 has cone shaped protrusions 12' integrally formed therewith. Such protrusions 12' may also be referred to as nano-grass or surface roughness. Each protrusion 12' has a radius of curvature (r) that is very small, ranging from about 0.1 nm to about 10 nm. The protrusions 12' are formed such that a valley 14 is formed at substantially flat areas of the substrate 12 where protrusions 12' are not formed, and crevices (not shown) may be formed in the region proximate two adjacent protrusions 12'. A plurality of crevices may resemble an ensemble of pits, each of which has a sharp point or angle (as opposed to the substantially flat areas shown in FIG. 1).

In an embodiment, the protrusions 12' may be formed by deep reactive ion etching and passivation. More specifically, the Bosch process may be used, and this process involves a series of alternating cycles of etching (e.g., using $SF_6$ and $O_2$ plasmas) and passivation (e.g., using a $C_4F_8$ plasma). The morphology of the resulting protrusions 12' may be controlled by controlling the conditions (e.g., vacuum pressure, RF power, total processing time, individual etching cycle time, individual passivation cycle time, and gas flow rates) of the process. In one non-limiting example, the etcher is operated at a pressure of 15 mTorr, the coil and platen powers of the etcher are 800 W and 10 W, respectively, each etching cycle (with $SF_6$ and $O_2$) is 6 seconds, each passivation cycle (with $C_4F_8$) is 5 seconds, and the flow rates for $SF_6$, $O_2$, and $C_4F_8$ are 100 sccm, 13 sccm, and 100 sccm, respectively. More generally, the flow rate may be any rate up to about 100 sccm.

Regular or non-regular arrays of the protrusions 12' may be formed. The etching and passivation process previously described often results in a non-regular array. It is to be understood that in order to generate a regular array, a fabrication method, such as focused ion-beam, e-beam lithography, or optical lithography. It is believed that the cone-shaped protrusions 12' may be designed in a predetermined manner to enable the resulting device (shown in FIGS. 3D, and 4-6) to be sensitive to a targeted range on the Raman spectrum (e.g., capable of producing stronger signals in a particular wavelength).

Figure 2A:
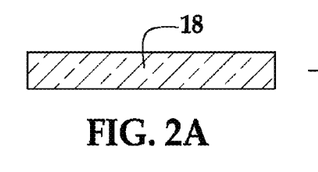
Figure 2B:
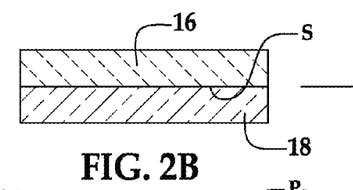
Figure 2C:
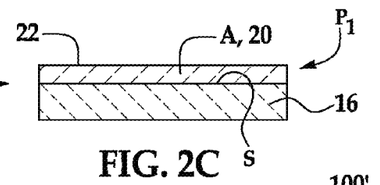
Figure 2D:
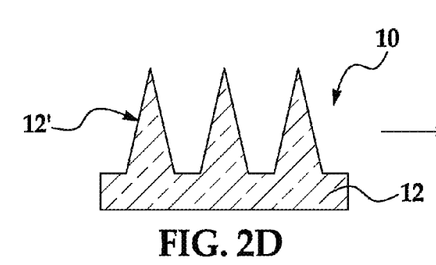
Figure 2E:
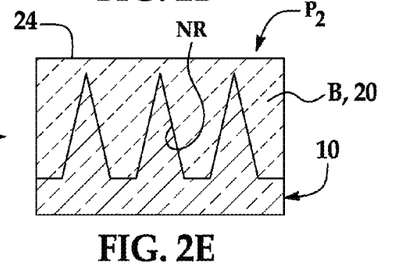
Figure 2F:
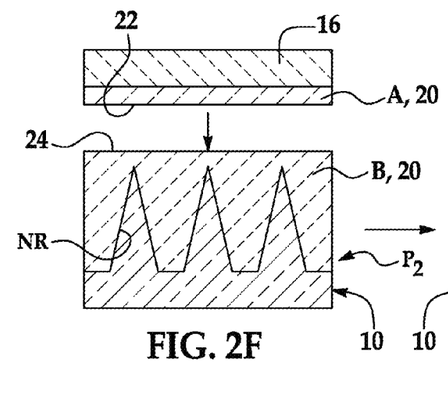
Figure 2G:
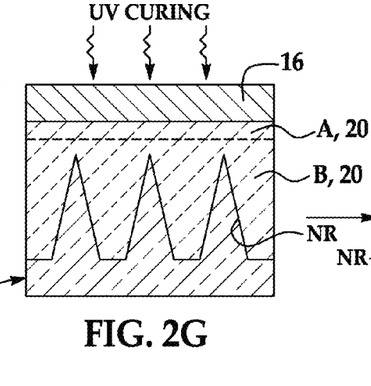
Figure 2H:
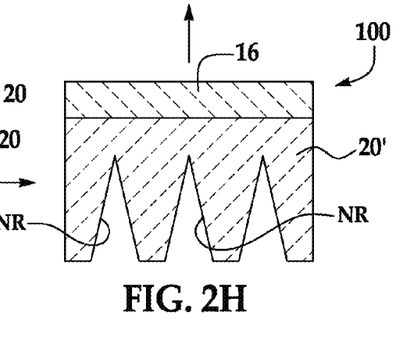
Figure 2I:
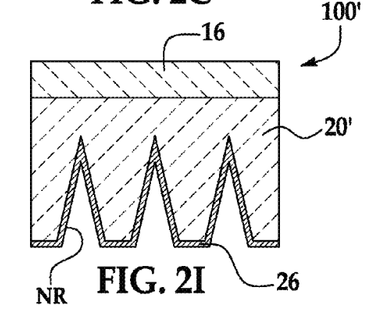

FIGS. 2A through 2I together illustrate the formation of the master mold 100, shown in FIG. 2I, using the template 10 (shown in FIG. 2D). FIGS. 2A through 2C illustrate the formation of a first portion $P_1$ of the mold 100, FIGS. 2D and 2E illustrate the formation of a second portion $P_2$ of the mold 100, and FIGS. 2F through 2I illustrate the combining of the first and second portions $P_1$, $P_2$ to form the master mold 100.

At the outset of the method for creating the mold 100, as shown in FIGS. 2A and 2B, a substantially flat film 16 is formed on a removable substrate 18. Any substrate 18 (e.g., any wafer) of any suitable dimensions and thickness may be selected, as long as the substrate 18 is removable from the material selected to form the film 16, and has a planar surface, so that the resulting substantially flat film 16 is also planar (i.e., does not have a pattern formed therein). A non-limiting example of a suitable substrate 18 is silicon. Other suitable examples include those listed for the substrate 12 discussed hereinabove.

The substantially flat film 16 is formed of a material that is transparent to ultraviolet radiation (i.e., wavelengths ranging from 320 to 380 nanometers). One non-limiting example of such a material includes polydimethylsiloxane (PDMS). Furthermore, any UV transparent and flexible polymer (i.e., capable of being flexed or bent without breaking) in the silicone family (e.g., PVC) may be used to form the substantially flat film 16. The transparent UV material is generally in the form of a liquid and can be deposited on the substrate 18 via pouring, spray coating, casting, or the like. In one embodiment, the thickness of the material deposited to form the film 16 ranges from about 5 µm to about 50 mm. Once deposited, the transparent UV material is allowed to harden, for example, in air or under heat (e.g., at 75° C. for about 2 hours, or at 120° C. for about 20 minutes), to form the film 16.

Since the substrate 18 has a planar surface, the resulting film 16 will also be planar. It is to be understood, however, that in some rare instances the substantially flat film 16 may have minor and sporadic irregularities on the surface S which transfer from the substrate 18 during formation of the film 16.

The film 16 may then be removed from the substrate 18. Since the film 18 does not stick to the substrate 18, the film 16 may be peeled off of the substrate 18.

A first portion A of an ultraviolet curable resist 20 is then deposited on the film 16. Since the ultraviolet curable resist 20 is ultimately used to generate the negative replica of the desirable cone-shaped pattern in the mold 100, the resist 20 is selected to have a sufficient rigidity to be able to conform to, and to duplicate/replicate with precision, the cone-shaped protrusions 12' of the template 10. As illustrated in the Example provided herein, any resist may not be selected, as not all resist can replicate the ultra-fine features of the cone-shaped protrusions 12' disclosed herein. Suitable ultraviolet curable resists 20 for the embodiments disclosed herein include a photoinitiator (i.e., a compound that generates a radical in response to UV radiation exposure), a cross-linking agent, and a siloxane based backbone chain. Non-limiting examples of suitable photoinitiators include azobisisobutyronitrile (AIBN), IRGACURE® 184 and IRGACURE® 810 (commercially available from BASF Corp., Florham Park, N.J.), and non-limiting examples of the cross-linking agent includes various species having more than one double or triple bond that opens up and polymerizes upon curing. In one embodiment, additional solvents are not included such UV curable resists 20, at least in part because of the presence of the siloxane based backbone. The siloxane based backbone may include double bonded terminal functional groups, such as acryls.

The components of the UV resist 20 are included in a predetermined ratio of photoinitiator to cross-linking agent to siloxane backbone. Each component can be present in a range of 0.05% to 99.9% of the total weight of the resist 20. In one embodiment, the UV resist 20 includes from about 0.5 wt % to about 2 wt % of the radial initiator, from about 88 wt % to about 92 wt % of the UV curable monomer species (i.e., the siloxane based backbone chain), and from about 7 wt % to about 11 wt % of the cross-linking agent. In one non-limiting example, the UV resist 20 includes 1 wt % of the radial initiator, 90 wt % of the UV curable monomer species (i.e., the siloxane based backbone chain), and 9 wt % of the cross-linking agent. Commercially available resists that may be used for the curable resist 20 include NXR-2010 (Nanonex Corp., Monmouth Junction, N.J.), and AR-UV-01 (Nanolithosolution, Inc., San Marcos, Calif.).

The first portion A of the UV curable resist 20 may be deposited on the film 16 via any suitable technique, such as spin coating, drop coating, dip-coating, or the like. The thickness of the first portion A ranges from about 20 nm to about 10 µm. Furthermore, as shown in FIG. 2C, the deposited first portion A of the UV curable resist 20 has a substantially planar surface 22.

The formation of the second portion $P_2$ is shown in FIGS. 2D and 2E. As illustrated in FIG. 2D, the template 10 is utilized in the formation of the second portion $P_2$. A second portion B of the UV curable resist 20 is deposited onto the template 10 such that the second portion B conforms to the shape of, and covers, each of the cone-shaped protrusions 12'. As such, a negative replica NR of the pattern of the cone-shaped protrusions 12' is formed in the second portion B of the curable resist 20. The second portion B is also deposited to extend above the tips of each of the protrusions 12' so that a substantially planar surface 24 is formed. As such, the thickness of the second portion B of the UV resist will depend, at least in part, on the height of the protrusions 12'. The second portion B may be deposited using the same techniques that are suitable for depositing the first portion A of the UV curable resist 20.

Once the first and second portions $P_1$, $P_2$ are formed, the steps for forming the master mold 100 are performed. These steps are illustrated in FIGS. 2F through 2I. As illustrated in FIG. 2F, the first portion $P_1$ is aligned with the second $P_2$ so that the surfaces 22, 24 will be in contact when the first portion $P_1$ is placed on the second portion $P_2$. In some instances, the first and second portions $P_1$, $P_2$ will have the same dimensions so that all of the surface 22 is in contact with all of the surface 24. In other instances, the dimensions of one of the portions $P_1$, $P_2$ may be smaller than the dimensions of the other portion $P_2$, $P_1$ so that the entire surface 22, 24 of the one portion $P_1$, $P_2$ contacts a portion of the surface 24, 22 of the other portion $P_2$, $P_1$.

When aligned and placed into contact, the first and second portions A, B of the UV curable resist 20 are able to intermingle at the interface of the two surfaces 22, 24. The same UV curable resist 20 is selected for both the first and second portions A, B, so that the materials join together when in contact, and so that curing results in the formation of a single cured resist 20' (see FIG. 2H). While the surfaces 22, 24 are in contact, ultraviolet radiation (in the form of light) is directed toward the portions A, B of the curable resist 20 at least through the film 16. Since the film 16 is formed of a UV transparent material, the ultraviolet radiation passes through the film 16 and cures the curable resist 20, thereby forming a single UV cured resist 20'. It is to be understood that the UV radiation may also be directed toward the resist 20 at any other desirable angle. Any suitable source of UV radiation may be used to initiate curing, such as, for example, UV lamps or plasma torches or lasers operating in the UV range. The actual wavelength (within the UV range of 320 nm to 380 nm) and intensity of the ultraviolet radiation used may vary, depending at least in part, upon the UV curable resist 20 selected.

As illustrated in FIG. 2H, the mold 100 includes the film 16 attached to the cured resist 20'. After curing, the mold 100 is formed and is removed from the template 10. The materials of the template 10 and the UV cured resist 20' are not adhered to one another after curing, and thus removal may be accomplished by peeling the mold 100 off of the template 10.

The cured resist 20' has the negative replica NR of the pattern of the cone-shaped protrusions 12' of the template 10. As previously mentioned, the resist 20, 20' has sufficient rigidity to replicate the sub-10 nm radius of curvature as well as the larger features (e.g., the base diameter) of the cone-shaped protrusions 12' in the form of a negative replica NR.

As shown in FIG. 2I, the mold 100 (shown as 100' in this Figure) also includes a release layer 26. This layer 26 is used to ensure that adhesion to subsequent molded materials does not result. It is to be understood that the adhesion layer 26 may be used even when the mold 100, 100' is to be subsequently used to pattern materials that will not likely adhere to the UV cured resist 20'. The thin release layer 26 is coated on the side of the cured resist 20' having the negative replica NR of the pattern of cone-shaped protrusions formed therein. The release layer 26 is conformally deposited on the negative replica NR of the cone-shaped pattern such that the sub-10 nm tip radius of curvature is not lost for any of the negatively replicated cones. It is to be understood that the height and diameter of the negatively replicated cones may be slightly reduced by the addition of the release layer 26. Such a reduction will depend upon the thickness of the release layer 26. However, in an embodiment, the thickness of the release layer 26 is on the order of one molecule thick (i.e., about 2 nm), and thus will not deleteriously affect the thickness of the features of the negative pattern (or the resulting cones formed therefrom). The release layer 26 is a self-assembled monolayer (SAM) generated via suitable SAM-forming techniques. In one embodiment, the release layer 26 is (1H,1H,2H,2H-perfluorooctyl)trichlorosilane (FOTS). The release layer 26 essentially adds a non-stick coating to the mold 100' so that the mold 100' does not subsequently adhere to materials being patterned therewith. It is to be understood that the release layer 26 is added when the material(s) to be patterned with the mold 100' will adhere to the UV cured resist 20' and/or when it is desirable to ensure that the mold 100' may be used for a variety of materials (even those that are unlikely to stick, as previously mentioned).

Figure 3A:
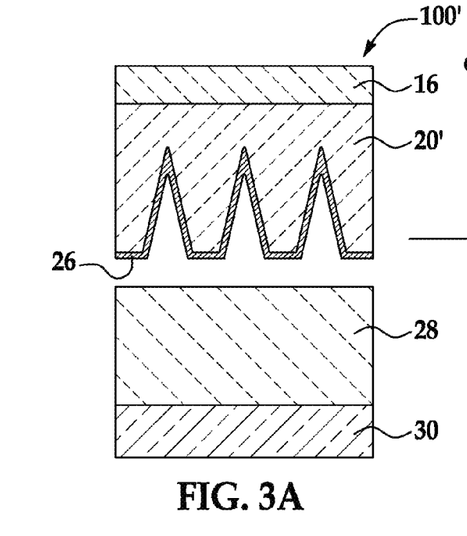
FIGS. 3A through 3D are semi-schematic cross-sectional views which together depict an embodiment of a method for forming an embodiment of a surface-enhanced Raman spectroscopy device.
Figure 3B:
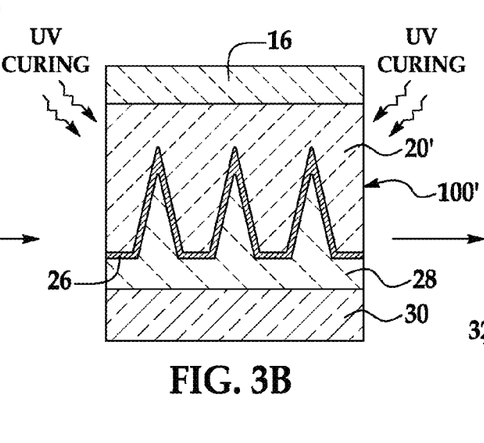
Figure 3C:
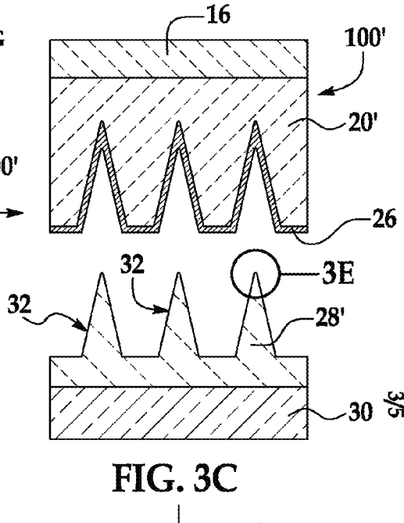
Figure 3D:
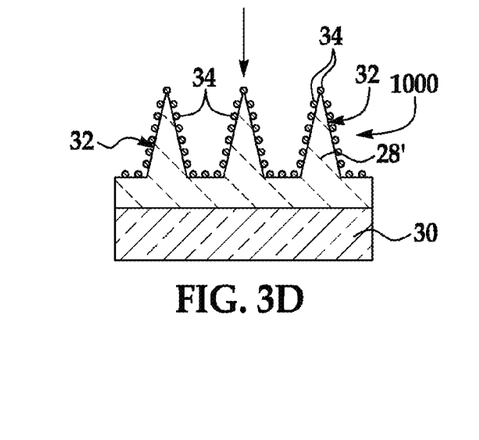

The mold 100 or 100' may then be used make a surface-enhanced Raman spectroscopy device 1000 (shown in FIG. 3D). FIGS. 3A through 3D illustrate an embodiment of the method for making such a device 1000.

As shown in FIG. 3A, an ultraviolet curable resist 28 that is to subsequently be patterned is established on a substrate 30. Non-limiting examples of suitable substrate 30 materials include single crystalline silicon, polymeric materials (acrylics, polycarbonates, polydimethylsiloxane (PDMS), polyimides, poly(acetylene)s, poly(pyrrole)s, poly(thiophene)s, polyanilines, poly(p-phenylene sulfide), and poly(para-phenylene vinylene)s (PPV), etc.), metals (aluminum, copper, stainless steel, alloys, etc.), quartz, ceramic, sapphire, silicon nitride, glass, silicon-on-insulators (SOI), or diamond like carbon films. Flexible materials may also be desirable for the substrate 30, so that the resulting device 1000 is flexible and can be rolled up. Non-limiting examples of flexible materials include thermoplastic polyolefin substrates, such as polyethylene or polypropylene, or a polyimide substrate.

The substrate 30 may have any desirable dimensions. In particular, the substrate 30 may be small enough to fabricate a single device 1000 or may be large enough to fabricate a plurality of devices 1000 thereon.

The resist 28 that is selected to be deposited on the substrate 30 is an ultraviolet curable resist that is capable of replicating the ultra-fine features of the negative replica NR of the mold 100 or 100'. As such, in one embodiment, the resist 28 is the same ultraviolet curable resist 20 used to form the mold 100, 100'. The resist 28 may be deposited using a roller coating process, or any of the techniques previously described for depositing the resist 20. The deposited resist 28 has a thickness such that the mold 100, 100' may be pressed therein enough to transfer the pattern of the mold 100, 100'

(e.g., negative replica NR) to the resist 28. As such, in one embodiment, the thickness of the resist 28 corresponds with the height of the cones in the negative replica NR, and thus is up to 2 μm thick. It is to be understood that the thickness of the resist 28 may be thicker if the height of the cones in the negative replica NR of the cone-shaped pattern is greater, and/or if it is desirable that a portion of the resist 28 remain unpatterned (see, e.g., FIG. 3D where the pattern does not extend through the resist 28 to the underlying substrate 30).

As shown in FIG. 3B, the mold 100, 100' is then pressed into the UV curable resist 28 so that the resist 28 conforms to the pattern of the mold 100, 100'. While the mold 100, 100' is pressed into the UV curable resist 28, ultraviolet radiation (in the form of light) is directed toward the curable resist 28. It is to be understood that the UV radiation may be directed toward the resist 28 from any desirable angle and from any desirable source (such as those previously discussed), as long as the resist 28 is exposed to the radiation and curing is accomplished. The wavelength and intensity of the ultraviolet radiation used may vary, depending at least in part, upon the UV curable resist 28 selected. In one embodiment, the resist 28 is exposed to UV light for a time ranging from about 10 seconds to about 20 minutes.

Figure 3E:
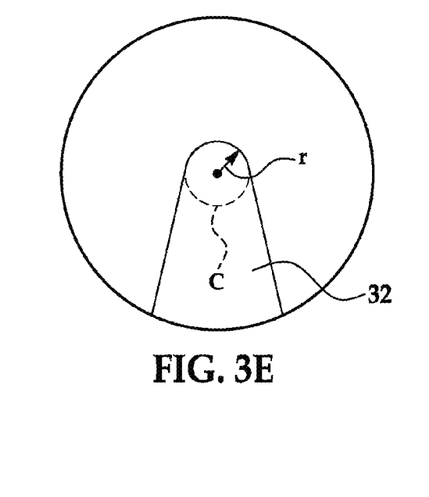
FIG. 3E is an enlarged view of one of the protrusions of FIG. 3C, illustrating the radius of curvature (r) of the protrusion.

Curing sets the negative replica NR pattern of the mold 100, 100' into the cured resist 28' such that the pattern transferred to the cured resists 28' resembles the pattern of the template 10. As such, the patterned cured resist 18' has cone-shaped protrusions 32 which have a radius of curvature, r, equal to or less than 10 nm. Referring briefly to FIG. 3E, an enlarged view of the cross-section of the tip of one of the protrusions 32 is shown. The radius of curvature, r, is also shown. In particular, the radius of curvature, r, is the radius of the approximate circle C that results when points are drawn on part of the curved portion of the 32. As previously mentioned, the pattern and dimensions of the cone-shaped protrusions 32 are transferred from the original template 10 using the mold 100 or 100'.

As illustrated in FIG. 3C, after curing, the mold 100' is removed from the patterned and cured resist 28' (which remains on substrate 30). In this particular non-limiting example, the cured resist 28' is made of the same material as the cured resist 20' of the mold 100', and thus the mold 100' with the release layer 26 is utilized to ensure that the resists 20, 28 do not adhere together during curing. This release layer 26 also enables the mold 100' to simply be lifted or peeled off of the patterned cured resist 28'.

The mold 100 (i.e., without the release layer 26) may be used when the cured resist 20' of the mold 100 is not the same as and will not adhere to the material used for the curable resist 28 during curing. When mold 100 is used, removal of the mold 100 may also be accomplished via lifting or peeling, or by etching away or dissolving the mold 100. Etching or dissolution may be accomplished using etchants or solvents that eat away at the mold 100 materials, but will not deleteriously affect the cured resist 28'. The etchant or solvent used will depend upon the mold 100 material. In an embodiment, a buffer oxide etch (BOE) or a potassium hydroxide (KOH) etchant is used.

Once the patterned cured resist 28' is formed, a Raman signal-enhancing material 34 is coated on the cone-shaped protrusions 32. It is to be understood that the phrase "Raman signal-enhancing material" as used herein means a material that, when established on the protrusions 32, is capable of increasing the number of Raman scattered photons when an analyte (or other material of interest) is located proximate to that protrusion 32, and when the analyte and material are subjected to electromagnetic radiation. Raman signal-enhancing materials include, but are not limited to, silver, gold, and copper.

The Raman signal-enhancing material 34 may be established by any suitable deposition or other coating technique. A blanket deposition technique may be used so that the material 34 is established on all of the exposed portions of the cured resist 28' (see, e.g., FIG. 5). As a non-limiting example, the material 34 may be deposited via electron-beam (e-beam) evaporation or sputtering. In still another non-limiting example, the Raman signal-enhancing material 34 can be pre-formed nanoparticles (e.g., of silver, gold, copper, etc.), which are coated onto the cured resist 28' (see FIGS. 3D, 4 and 6). Such nanoparticles have an average diameter ranging from about 1 nm to about 10 nm. It is believed that the presence of the material 34 nanoparticles (rather than a continuous coating of material 34) at the apex further enhances the electric field during SERS operation. The material 34 itself may also have a surface roughness that spontaneously forms during the deposition process. Such surface roughness can act as additional optical antennas to increases the SERS-active sites over each protrusion 32 and/or adjacent each protrusion 32.

After deposition of the material 34, each protrusion 32 remains substantially unchanged in terms of its tip/apex angle and radius of curvature r, and in terms of any crevice angles, as a relatively uniform coating (often in the form of numerous small nanoparticles on the slopes and/or tips of the protrusions 32) of the material 34 is produced.

Figure 5:
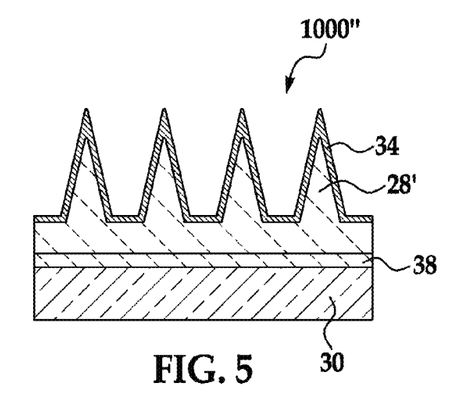
FIG. 5 is a semi-schematic cross-sectional view of yet another embodiment of the surface-enhanced Raman spectroscopy device.
Figure 6:
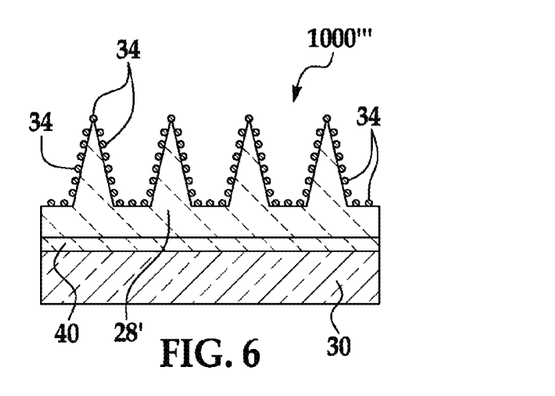
FIG. 6 is a semi-schematic cross-sectional view of still another embodiment of the surface-enhanced Raman spectroscopy device.

It is to be understood that the device 1000 disclosed herein may, in some embodiments, include additional components, such as, for example, a grating structure 36 (see FIG. 4), a reflective layer 38 (also referred to as a mirrored structure, see FIG. 5), and/or an adhesive layer 40 (see FIG. 6). Such additional components may be used alone (as shown in FIGS. 4 through 6) or in any combination in a single device 1000, for example, a grating and a reflective layer may be incorporated into the same device 1000 (not shown).

Figure 4:
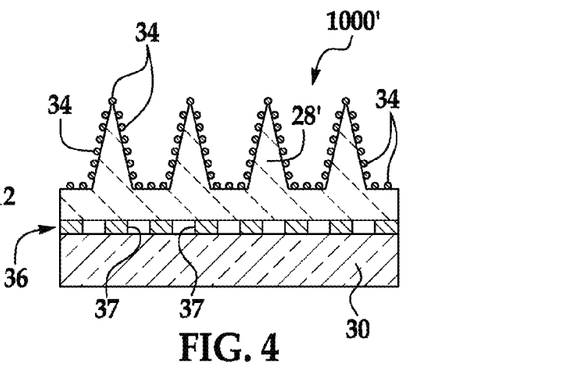
FIG. 4 is a semi-schematic cross-sectional view of another embodiment of the surface-enhanced Raman spectroscopy device.

Referring now specifically to FIG. 4, the device 1000' includes the grating structure 36 positioned between the substrate 30 and the cured resist 28'. During formation of such a device 1000', the grating structure 36 is formed on the substrate 30 prior to depositing the curable resist 28 thereon, imprinting the curable resist 28 via the mold 100, 100', and curing the patterned curable resist 28. The grating layer 36 may be a dielectric or metal layer having grating holes or openings 37 formed therein. Non-limiting examples of such grating structures 36 and how they are formed are described in U.S. patent application Ser. No. 12/771,753, filed on Apr. 30, 2010, entitled "ENHANCING SIGNALS IN SURFACE ENHANCED RAMAN SPECTROSCOPY (SERS)", which is incorporated herein by reference in its entirety.

Referring now specifically to FIG. 5, the device 1000" includes the reflective layer 38 positioned between the substrate 30 and the cured resist 28'. During formation of such a device 1000", the reflective layer 38 is formed on the substrate 30 prior to depositing the curable resist 28 thereon, imprinting the curable resist 28 via the mold 100, 100', and curing the patterned curable resist 28. The reflectivity of such a reflective/mirrored layer 38 is generally above 90%. As such, any metal having this reflectivity may by used, including, but not limited to gold. Such a layer 38 may be deposited via electron beam (e-beam) evaporation, sputtering, or the like. A suitable thickness for the layer 38 generally ranges from about 5 nm to about 5 mm. Non-limiting examples of such reflective/mirrored layers 38 are described in U.S. patent application Ser. No. 12/771,824, filed on Apr. 30, 2010, entitled "APPARATUS FOR PERFORMING SERS", which is incorporated herein by reference in its entirety. While the reflective/mirrored layer 38 shown in FIG. 5 is substantially planar, a concave reflective/mirrored layer 38 may be included instead. Such concave reflective/mirrored layers 38 are described in U.S. patent application Ser. No. 12/771,753 filed on Apr. 30, 2010, entitled "ENHANCING SIGNALS IN SURFACE ENHANCED RAMAN SPECTROSCOPY (SERS)"(already incorporated by reference herein).

Referring now specifically to FIG. 6, the device 1000''' includes the adhesive layer 40 positioned between the substrate 30 and the cured resist 28'. During formation of such a device 1000''', the adhesive layer 40 is formed on the substrate 30 prior to depositing the curable resist 28 thereon, imprinting the curable resist 28 via the mold 100, 100', and curing the patterned curable resist 28. The adhesive layer 40 may be formed of a metal or 3-acryloxypropyl trichlorosilane. In one embodiment, the adhesive layer 40 is a self-assembled monolayer (SAM) that is a single molecule thick. Generally, the thickness of the adhesive layer ranges from about 0.5 nm to about 5 nm, and is used to strengthen the adhesion of the substrate 30 to the cured resist 28'. It is to be understood that the adhesive layer 40 may be used in any embodiment in which it is not desirable to remove the cured resist 28' from the substrate 30. The addition of adhesive layer 40 aids in the adhesion between these two components 28' and 30.

Figure 7:
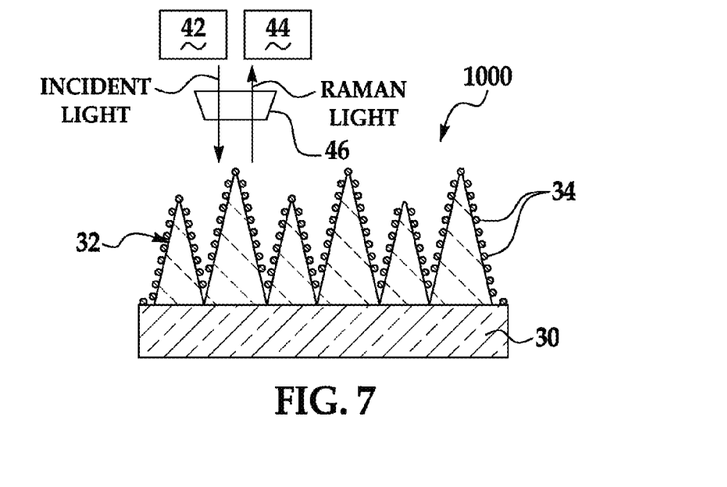
FIG. 7 is a semi-schematic cross-sectional view of a system for performing surface-enhanced Raman spectroscopy.

FIG. 7 illustrates components that are used in conjunction with the device 1000 (or any other embodiment of the devices 1000', 1000'', 1000''' disclosed herein) in order to perform Raman spectroscopy. Such additional components include a stimulation/excitation light source 42, and a detector 44. In some instances, the additional components also include an optical component (e.g., optical microscope 46), which is positioned between the light source 42 and the device 1000. The optical component 46 focuses the light from the light source 42 to a desirable area of the device 1000, and then again collects the Raman scattered light and passes such scattered light to the detector 44. Analyte molecules (not shown) may be introduced across the Raman active structures protrusions 32, where they may be exposed to stimulating/excitation wavelengths from the light source 42, and the resulting signals may be detected by the Raman detection unit 44. It is believed that the total surface area of the cone-shaped protrusions 32 enables a large number of target molecules to be trapped on the substrate device 1000, and thus more Raman photons can contribute to the overall SERS signal.

In certain embodiments, the detector 44 may also be operably coupled to a computer (not shown) which can process, analyze, store and/or transmit data on analytes present in the sample.

While not shown in all embodiments, it is to be understood that a release layer may be used during any of the steps of the method disclosed herein which involve peeling of one material from another. For example, a release layer may be used at the interface of the substrate 12 and the second portion B of the resist 20 when forming the second portion $P_2$ of the mold 100, 100'.

To further illustrate embodiment(s) of the present disclosure, an example is given herein. It is to be understood that this example is provided for illustrative purposes and is not to be construed as limiting the scope of the disclosed embodiment(s).

EXAMPLE

Template Formation

Templates were formed using crystalline silicon substrates. The cone-shaped protrusions were fabricated using the Bosch process. In particular, an STS (Surface Technology Systems) etcher was used for the etching of silicon wafers of six inches diameter. No prior cleaning was used for the silicon wafers. The etcher was operated at a pressure of 15 mTorr, and the coil and platent powers were 800 W and 10 W, respectively. Each cycle of etching (with $SF_6$ and $O_2$) and passivation (with $C_4F_8$) was 6 seconds and 5 seconds, respectively. The flow rates for $SF_6$, $O_2$ and $C_4F_8$ were 100 sccm, 13 sccm and 100 sccm, respectively. SEM images of the template are shown in FIGS. 8A and 8B. The average radius of curvature of the cones was 10 nm or less.

Mold and Comparative Mold Formation

The mold fabricated in accordance with the embodiments disclosed herein included two portions that were adhered together. The first portion was a UV nanoimprint resist (with a thickness between 1 and 2 μm) formulated according to an embodiment disclosed herein and coated on a polydimethylsiloxane (PDMS) planar film, and the second portion was the same UV curable resist (with a thickness between 1 and 2 μm) coated to cover the cone-shaped protrusions of one of the templates. The UV curable resist layers of each of the portions were put in contact with each other and cured by exposing them to a UV lamp for 15 minutes. After curing the mold was removed from the template. A release layer of 1H,1H,2H,2H-perfluorooctyl)trichlorosilane was formed using a self-assembling technique on the negatively patterned portion of the mold.

The comparative mold was fabricated by pouring space grade PDMS elastomer onto another of the templates. The PDMS elastomer was allowed to harden (by exposing it to heat in an oven), and then was removed from the template.

SERS Substrate Formed with Mold

Figure 9A:
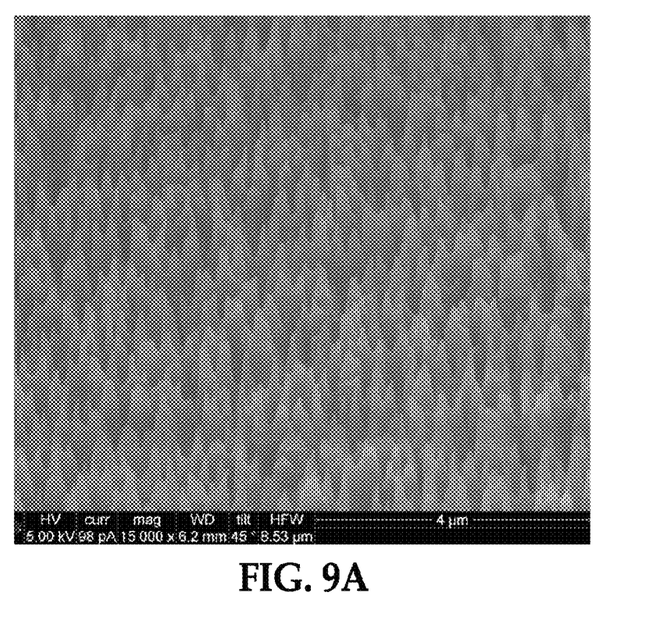
FIGS. 9A and 9B are SEM images (at 15000× and 250000× magnification, respectively) of cone-shaped protrusions formed via nanoimprint lithography using the mold formed from the ultraviolet resist disclosed herein.
Figure 9B:
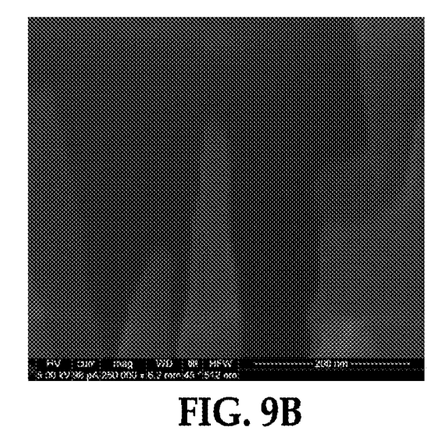

A UV curable resist (i.e., AR-UV-01) was spin coated onto a planar silicon substrate. The mold (fabricated in accordance with the embodiments disclosed herein) was pressed into the AR-UV-01 UV curable resist. While the mold was pressed into the curable resist, the curable resist was exposed to ultraviolet radiation using a UV lamp. After curing, the mold was removed. The pattern of the mold was transferred to the cured resist without losing the ultra-fine features of the mold and original template. The resulting patterned substrate is shown in FIGS. 9A and 9B. As illustrated, the sub-10 nm features from the original template were transferred using the UV resist mold disclosed herein.

Comparative SERS Substrate Formed with Comparative Mold

Figure 10A:
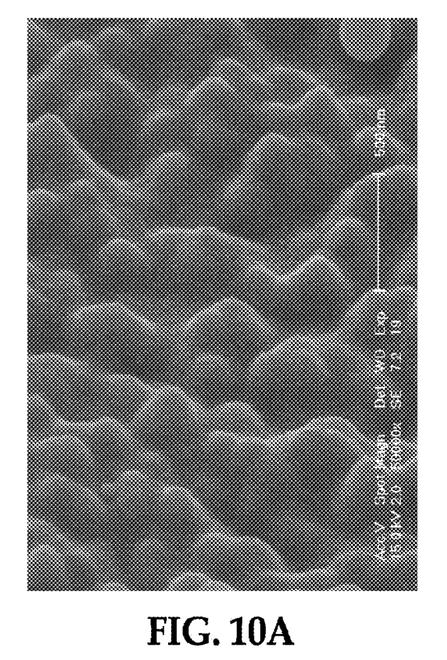
FIGS. 10A and 10B are SEM images at 50000× magnification and 65000× magnification, respectively, of cone-shaped protrusions formed in Norland Optical Adhesive 83H ("NOA83H") via nanoimprint lithography using the polydimethylsiloxane mold.
Figure 10B:
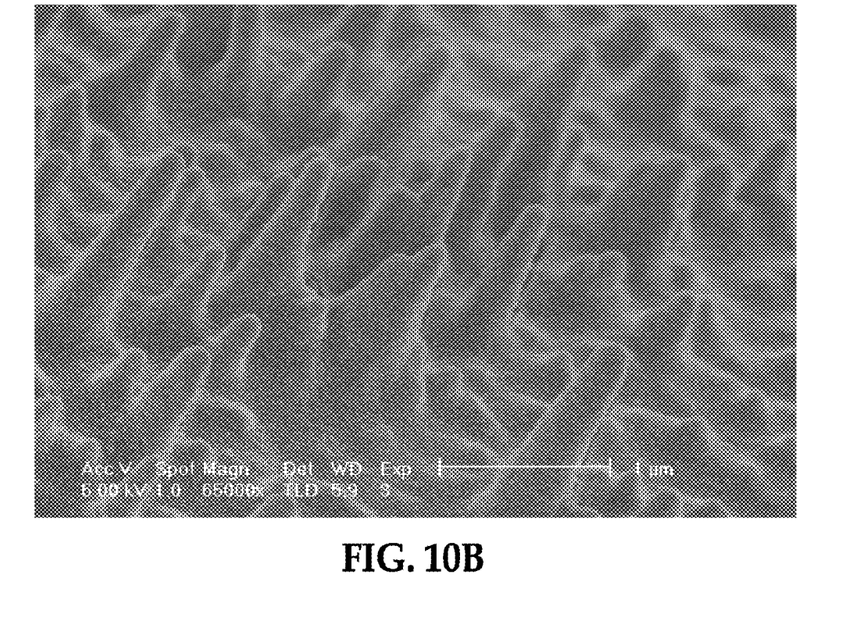

Norland Optical Adhesive 83H ("NOA83H") was spin coated on a silicon substrate. The comparative mold was pressed into the NOA83H resist. While the comparative mold was pressed into the NOA83H resist, the NOA83H resist was exposed to ultraviolet radiation using a UV lamp. After curing, the comparative mold was removed. The resulting patterned substrate is shown in FIGS. 10A and 10B. As illustrated (especially when comparing FIGS. 9A and 9B with FIGS. 10A and 10B), the ultra-fine features of the original template were not duplicated using PDMS as the mold.

It is to be understood that the ranges provided herein include the stated range and any value or sub-range within the stated range. For example, a weight percent (wt %) range of approximately 1 wt % to about 20 wt % should be interpreted to include not only the explicitly recited weight percent limits of 1 wt % to 20 wt %, but also to include individual weight percentages, such as 2 wt %, 3 wt %, 4 wt %, etc., and sub-ranges, such as 5 wt % to 15 wt %, 10 wt % to 20 wt %, etc.

While several embodiments have been described in detail, it will be apparent to those skilled in the art that the disclosed embodiments may be modified. Therefore, the foregoing description is to be considered exemplary rather than limiting.

What is claimed is:

1. A surface-enhanced Raman spectroscopy device, comprising:
   a substrate;
   an ultraviolet cured resist disposed on the substrate and having a pattern of cone-shaped protrusions, each cone-shaped protrusion of the pattern having a tip with a radius of curvature equal to or less than 10 nm, and the ultraviolet cured resist formed of a predetermined ratio of a photoinitiator, a cross-linking agent, and a siloxane based backbone chain; and
   a Raman signal-enhancing material disposed on each of the cone-shaped protrusions.

2. The device as defined in claim 1 wherein the substrate is a flexible substrate selected from a thermoplastic olefin substrate or a polyimide substrate.

3. The device as defined in claim 1, further comprising a grating structure disposed between the substrate and the ultraviolet cured resist.

4. The device as defined in claim 1, further comprising a reflective layer disposed between the substrate and the ultraviolet cured resist.

5. The device as defined in claim 1, further comprising:
   a reflective layer disposed directly on the substrate; and
   a grating structure disposed directly on the reflective layer;
   wherein the ultraviolet cured resist is disposed on the grating structure.

6. The device as defined in claim 1, wherein each cone-shaped protrusion of has a height up to 2 μm and a base having a diameter up to 500 nm.

* * * * *

UNITED STATES PATENT AND TRADEMARK OFFICE
CERTIFICATE OF CORRECTION

PATENT NO. : 8,314,932 B2
APPLICATION NO. : 12/771440
DATED : November 20, 2012
INVENTOR(S) : Fung Suong Ou et al.

Page 1 of 1

It is certified that error appears in the above-identified patent and that said Letters Patent is hereby corrected as shown below:

In the Claims:

In column 12, line 13, in Claim 6, after "protrusion" delete "of".

Signed and Sealed this
Fourteenth Day of May, 2013

Teresa Stanek Rea
*Acting Director of the United States Patent and Trademark Office*